United States Patent [19]
Vandewalls

[11] Patent Number: 4,896,663
[45] Date of Patent: Jan. 30, 1990

[54] SELF CENTERING FEMORAL DRILL JIG

[75] Inventor: Mark V. Vandewalls, Pierceton, Ind.

[73] Assignee: Boehringer Mannheim Corporation, Indianapolis, Ind.

[21] Appl. No.: 258,018

[22] Filed: Oct. 14, 1988

[51] Int. Cl.⁴ ............................................. A61B 17/56
[52] U.S. Cl. ..................................... 606/79; 269/902; 269/236; 408/84; 408/97; 408/115 R; 408/105; 606/80; 606/85
[58] Field of Search .......... 128/92 VD, 92 VL, 92 V, 128/92 VZ; 408/103–106, 108, 84, 95, 97, 115 R; 623/23; 269/902, 218, 229, 236, 246

[56] References Cited

U.S. PATENT DOCUMENTS

| | | | |
|---|---|---|---|
| 378,196 | 2/1888 | Dunn | 408/87 |
| 449,494 | 3/1891 | Paquette et al. | 408/106 |
| 460,883 | 10/1891 | Nugent | 408/105 |
| 667,880 | 2/1901 | Hinckley et al. | 408/106 |
| 1,028,855 | 6/1912 | Blomstrom | 408/84 |
| 1,249,584 | 12/1917 | Wycislo | 408/84 X |
| 1,727,061 | 10/1927 | Hicks | 408/106 |
| 2,416,228 | 8/1944 | Sheppard | 408/105 |
| 4,224,669 | 9/1980 | Weber | 623/23 |
| 4,246,895 | 1/1981 | Rehder | 128/92 VV |
| 4,284,080 | 8/1981 | Rehder | 128/317 X |
| 4,341,206 | 6/1982 | Perrett et al. | 128/92 VD |
| 4,502,475 | 3/1985 | Welgle et al. | 128/92 VD |
| 4,672,957 | 6/1987 | Hourahane | 128/92 VD |

FOREIGN PATENT DOCUMENTS

| | | | |
|---|---|---|---|
| 679888 | 7/1939 | Fed. Rep. of Germany | 128/92 VD |
| 1033135 | 8/1983 | U.S.S.R. | 128/92 VD |
| 21545 | 9/1906 | United Kingdom | 408/84 |
| 19784 | 8/1912 | United Kingdom | 408/84 |
| 1448111 | 9/1976 | United Kingdom | 128/92 VD |

OTHER PUBLICATIONS

Siebrandt Manf., p. 3.

*Primary Examiner*—Robert A. Hafer
*Assistant Examiner*—Kevin G. Rooney
*Attorney, Agent, or Firm*—Perman & Green

[57] ABSTRACT

A hand-held drill jig is utilized to locate and maintain a central axis through a head and an associated neck of a femur enabling a blind hole to be drilled into the femoral head oriented to the central axis. The drill jig is adjustable to accommodate a broad range of sizes of femurs and can be readily attached to, then removed from, the femur. A positioning mechanism is provided to firmly engage both the outer peripheral surface of the femoral head and the femoral neck. This operation renders associated drill bushing immobile relative to the femur and orients its longitudinal axis with the central axis. A drill bit is then capable of being guided through the drill bushing and into cutting engagement with the femoral head.

5 Claims, 3 Drawing Sheets

SELF CENTERING FEMORAL DRILL JIG

BACKGROUND OF THE INVENTION

1. Field of the Invention

The present invention relates generally to surgical apparatus and, more particularly, to a hand held drill jig intended for use during surgery to locate and maintain a central axis through a femoral head and an associated femoral neck enabling a blind bore to be drilled into the femoral head oriented to the central axis.

2. Description of the Prior Art

There are instances which hip surgery does not require complete replacement of a femoral head. Instead, it is a relatively common procedure to somewhat reshape the femoral head, then attach a shell prosthesis covering the reshaped natural head. In some instances the shell prosthesis has a downwardly projecting pin so as to locate and hold the shell in proper position. Such a situation is disclosed in U.S. Pat. No. 4,246,895. In some other instances, as disclosed in U.S. Pat. No. 4,224,699, there is no downwardly projecting pin integral with the shell, but rather an appropriate screw which is used to fixedly mount the shell into position.

In either instance, it is necessary, or at least desirable, to provide a bore to receive the downwardly extending pin or screw. For this purpose, it has been common practice for the surgeon to drill into the femoral head from a superior position while firmly gripping the femur in one hand and operating an electric drill motor with the other hand without guides of any nature to aid him in the process. Thus, the axis of the resulting bore would be randomly disposed, as determined visually by the surgeon and further as determined by the steadiness with which he could manually maintain the relative positioning between the bone on one hand and the drill motor and its associated drill bit in the other hand.

SUMMARY OF THE INVENTION

It was in an attempt to alleviate this situation and the inaccuracies resulting from such a manual drilling process that the present invention was conceived and has now been reduced to practice. To this end, a hand-held drill jig is provided to locate and maintain a central axis. The drill jig is utilized to locate and maintain an orientation relative to a central axis through a head and associated neck of a femur enabling a blind hole to be drilled into the femoral head oriented to the central axis. The drill jig is adjustable to accommodate a broad range of sizes of femurs and can be readily attached to, then removed from, the femur. A positioning mechanism is provided to firmly engage both the outer peripheral surface of the femoral head and the femoral neck. This operation renders immobile relative to the femur an associated drill bushing and orients its longitudinal axis with the central axis. A drill bit is then capable of being guided through the drill bushing and into cutting engagement with the femoral head.

Features and benefits of the invention include it small, compact size and light weight which enable it to be used by a surgeon during the reconstruction procedure. It is easily operable and can be readily attached to a femur for the drilling operation and, when the operation has been completed, just as readily detached from the femur. Additionally, the drill jig of the invention is of simplified construction utilizing a minimum of parts thereby resulting in a relatively low initial cost and a low cost of maintenance can be similarly anticipated. Being constructed primarily of stainless steel and aluminum components and by reason of its small size, the drill jig of the invention is easily autoclavable which is a necessary attribute of any surgical instrument.

Other and further features, objects, advantages, and benefits of the invention will become apparent from the following description taken in conjunction with the following drawings. It is to be understood that both the foregoing general description and the following detail description are exemplary and explanatory but are not restrictive of the invention. The accompanying drawings, which are incorporated in and constitute a part of this invention, illustrate one embodiment of the invention and, together with the description, serve to explain the principles of the invention in general terms. Throughout the disclosure, like numerals refer to like parts.

DESCRIPTION OF THE PREFERRED EMBODIMENTS

Figure 1:
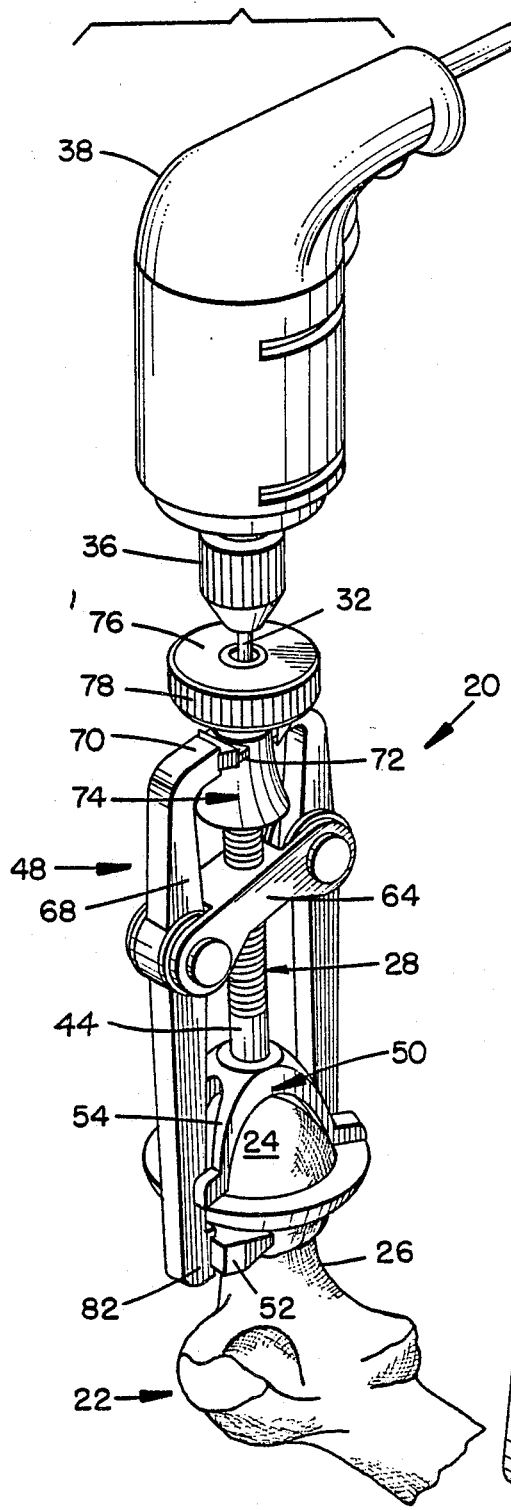
FIG. 1 is a perspective view illustrating a drill jig embodying the invention in actual use.

Turn now to the drawings and initially to FIGS. 1-4 which illustrates a hand-held drill jig 20 embodying the invention in firm engagement with a femur 22 intended to be operated upon. As will subsequently be more clearly described, the drill jig 20 is in firm engagement with the femur 22 at spaced locations, namely with the outer peripheral surface of the femoral head 24 and with the outer peripheral surface of the neck 26. An elongated guide bushing 28 of the drill jig 20 has a longitudinal axis 30 (FIG. 3) which is thereby oriented with a central axis of the femur extending through the head 24 and the neck 26. With this orientation of parts and components, a drill bit 32 is slidingly received in an internal longitudinal bore 34 (FIG. 3) of the guide bushing 28. The drill bit 32 is releasably fixed to a chuck 36 of an associated drill motor 38. The surgeon operates the drill motor 38 and in so doing advances the drill bit 32 through the guide bushing 28 toward and into cutting engagement with the femoral head 24.

In this manner, an accurately sized and positioned drill hole 40 is formed in the femur 22 in a more rapid and accurate manner than has previously been known. A detailed description of the drill jig 20 which achieves this desirable result will now be presented.

With continuing reference to FIGS. 1-4, it is seen that the drill bushing 28 is externally threaded for most of its length, specifically, from a proximal end 42 to an integral collar 44 which extends the remaining distance to a distal end 46 of the drill bushing.

Figure 5:
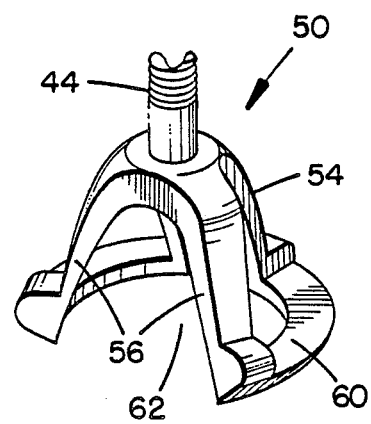
FIG. 5 is a detail perspective view showing one orientation of a component of the drill jig.
Figure 6:
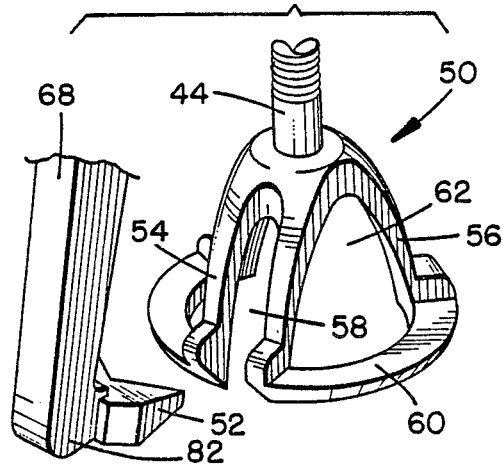
FIG. 6 is a detail perspective view showing another orientation of the component illustrated in FIG. 5 and its relationship with another component of the drill jig.

It was previously explained that the drill jig 20 is engageable with the femur 22 at spaced locations to enable the longitudinal axis of the drill bushing 28 to be oriented to the central axis through the head 24 and the neck 26. A positioning structure 48 will now be described which achieves this desirable result. This positioning structure 48 includes both a head cone 50 (FIGS. 5 and 6) for engageably receiving the femoral head 24 and a pair of opposed gripper members 52 for mutually, and firmly, engaging the outer peripheral surface of the femoral neck 26.

The head cone 50 is fittingly received on the collar 44 or fixed thereto in some other suitable fashion. In any event, it is seen to include a plurality of legs 54 and 56 extending away from the distal end 46 of the drill bushing 28 at circumferentially spaced locations and also extending away from the longitudinal axis 30. As seen particularly well in FIGS. 5 and 6, the legs 54 and 56 are not arranged at equally spaced circumferential locations around the collar 44. Rather, as illustrated, the pair of legs 54 is positioned relatively close together so as to define a slot 58 therebetween. A ring segment 60 integrally joins the extreme ends of each pair of legs 54 and 56 distant from the collar 44 so as to add strength and stability to the legs. However, there is no similar ring segment joining the tip ends of the legs 56, 56 in regions diametrically opposed to the slot 58. This deficiency serves to provide a desired entry into a cavity 62 defined by the head cone 50 for reception and eventual engagement of the femoral head 24. This construction will be more completely described below.

The positioning structure 48 also includes a cross beam 64 which has a central clearance hole 66 enabling it to be slidably received on the drill bushing 28 for movement generally between the proximal end 42 and the distal end 46. The cross beam 64 lies generally in a plane which is perpendicular to the longitudinal axis 30 and at its opposite ends distant from the drill bushing 28 serves to pivotally mount a pair of operating arms 68 for movement in the plane of the axis 30. Proximal ends 70 of the operating arms 68 are turned inwardly in the direction of the drill bushing 28 to the extremities of which are fixed, in a suitable manner, cam followers 72.

An internally threaded sleeve 74 is threadedly engaged with the drill bushing 28. An operating knob 76 which may have an outer peripheral knurled surface 78 is integral with the sleeve 74. Thus, when the operating knob 76 is rotated in one direction about the axis 30, it causes the sleeve 74 to advance in the direction of the distal end 46 (FIG. 3) and, conversely, when it is rotated in the opposite direction it causes the sleeve to advance toward the proximal end 42. As seen especially well in FIGS. 1-3, an outer peripheral surface 80 is positioned to engageably receive the cam followers 72 and is contoured to assure a desired motion of components of the drill jig 20 as will be described.

Figure 8:
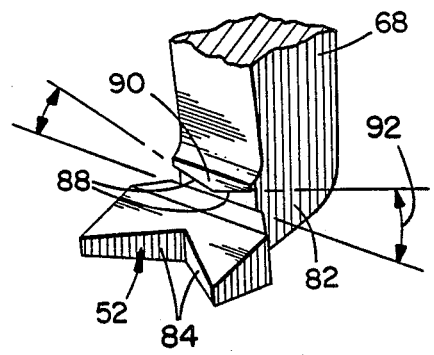
FIG. 8 is a detail perspective view of still another component of the drill jig.

The gripper members 52, previously mentioned, are suitably mounted to in-turned far ends 82 of the operating arms 68. The gripper members 52 may have v-shaped surfaces 84 (FIG. 8) for clamping engagement with the femoral neck 26. Preferably, each gripper member 52 is mounted on a stub shaft 86 which permits rotation about an axis generally transverse to the longitudinal axis 30. However, preferably, the extent of rotation of the gripper members is limited by means of stop surfaces 88 defined by an outwardly projecting shoulder 90, that is, projecting in the direction of the longitudinal axis 30. In a typical construction, the stop surfaces 88 may permit rotation through an arc of approximately 60 degrees as indicated by reference manual 92 in FIG. 8. In this manner, the v-surfaces 84 of the gripper members 52 can be assured an optimal orientation for gripping engagement with the femoral neck 26.

Figure 2:
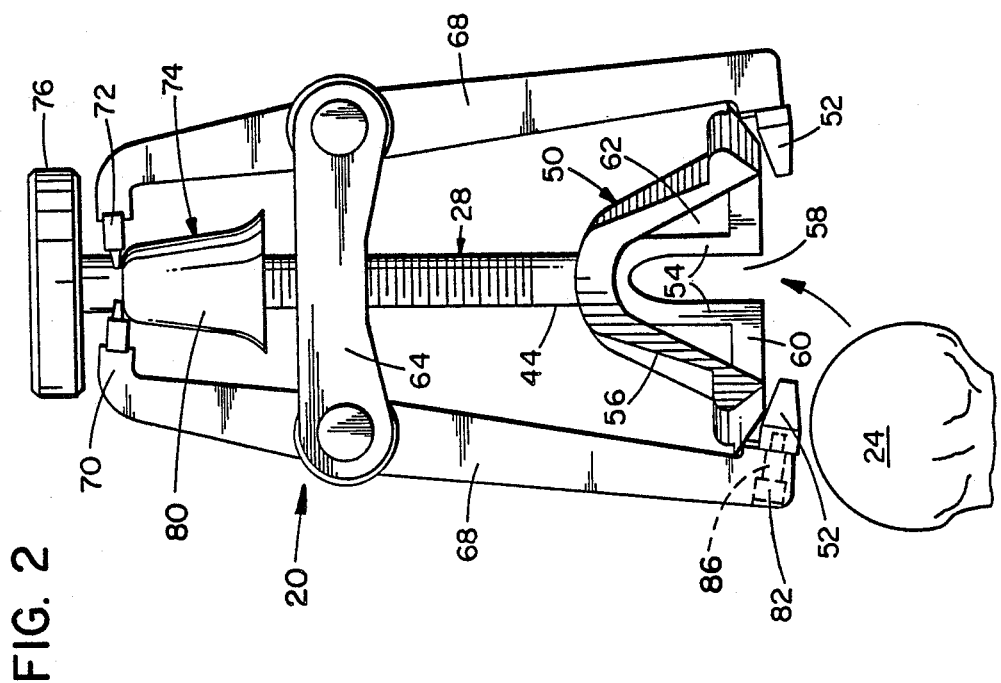
FIG. 2 is a front elevation view of the drill jig depicted in FIG. 1 and illustrating one orientation of certain components therein.
Figure 4:
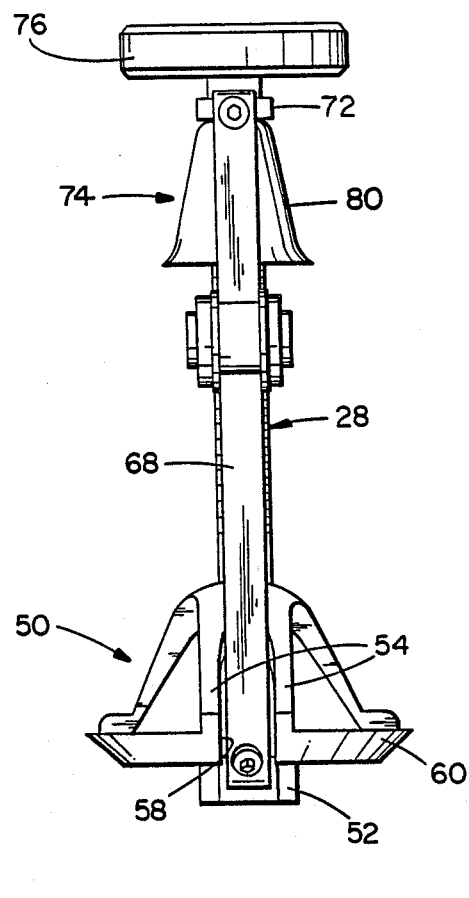
FIG. 4 is a side elevation view of the drill jig of the invention illustrated in FIG. 3.
Figure 7:
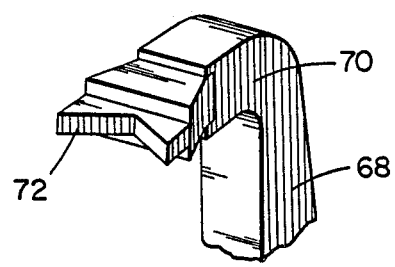
FIG. 7 is a detail perspective view of yet another component of the drill jig.

The operation of the drill jig 20 will now be described with particular reference to FIGS. 1 to 3.

In the course of the surgical procedure, the femoral head 24 will have been withdrawn from the acetabulum (not shown) to a sufficient extent to enable the drill jig 20 to be mounted on the femur 22. For this purpose, the head cone 50 is rotated about the axis 30 so as to orient its broad opening as defined between the legs 56 so as to be generally coextensive with the operating arms 68 (See FIG. 2). At this stage of the procedure, the sleeve 74 is moved to a location adjacent the proximal end 42 of the drill bushing 28 and the cross beam 64 is moved along the drill bushing to a position proximate to the sleeve 74 so as to enable the widest possible opening between the gripper members 52. Thereupon, the drill jig 20 is moved relative to the femur 22 so as to cause entry of the femoral head 24 into the cavity 62 defined by the head cone 50.

Figure 3:
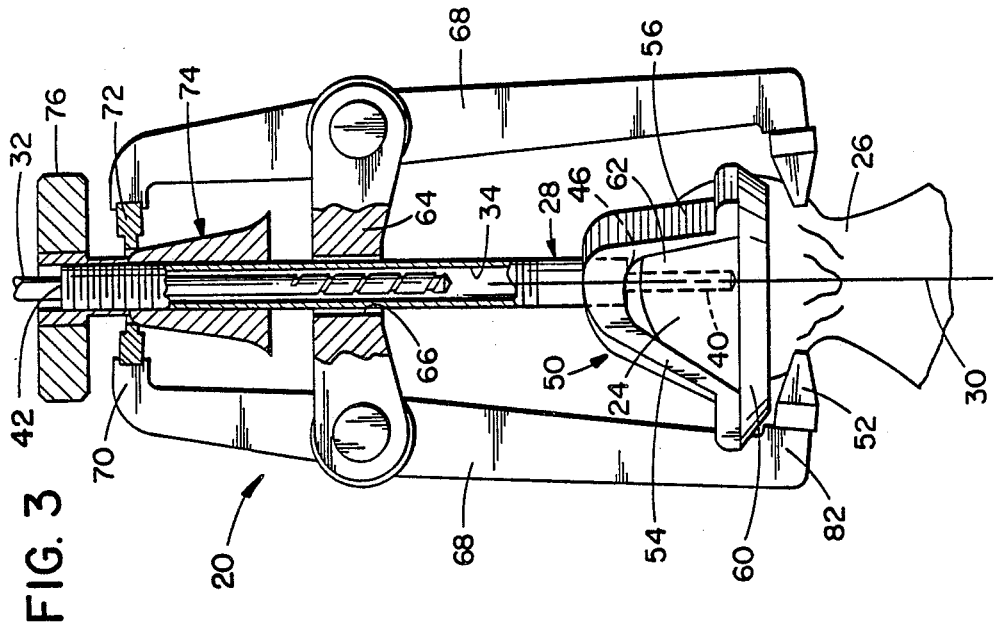
FIG. 3 is a front elevation view, similar to FIG. 2, certain parts being cut away and shown in section, illustrating another orientation of certain components therein.

Thereupon, as seen in FIG. 3, the head cone 50 is rotated approximately 90° about the axis 30 until the slot 58 is aligned with one of the operating arms 68, the thickness of the operating arms being slightly less than the width of the slot 58. The surgeon then moves the head cone 50 into engagement with the outer peripheral surface of the femoral head 24 and, simultaneously, positions the gripper members 52 so that they are generally coextensive with the femoral neck 26. In order to permit the swinging motion of the operating arms 68 so that the gripper members 52 move toward one another, it is necessary to advance the sleeve 74 toward the distal end 46 by means of the knob 76. Thereupon, with the v-surfaces 84 of the gripper members 52 manually held in gripping engagement with the femoral neck 26, the knob 76 is then rotated in an opposite direction to cause movement of the sleeve 74 once again in the direction of the proximal end 42. Thereupon, the cam followers 72 will engage the outer peripheral surface 80 of the sleeve 74 and by reason of the shape thereof, with continued movement of the sleeve 74 toward the proximal end 42, the v-surfaces 84 become ever more grippingly engaged with the femoral neck 26. The knob 76 continues to be rotated until the drill jig 20 is rendered immobile relative to the femur 22.

In this condition, the head cone 50 is tightly clamped onto the outer peripheral surface of the femoral head 24 and the gripper members 52 are tightly clamped into engagement with the femoral neck 26. By thus firmly holding the femur 22 at a pair of spaced locations along its length, the longitudinal axis 30 of the drill bushing 28 is thereby oriented relative to a central axis extending through the head 24 and through the neck on 26. In this manner, a proper orientation between the drill jig 20 and the femur 22 will have been achieved enabling the drilling operation to commence. Thereupon, the drill bit 32 is inserted into the bore 34 at the proximal end 42 of the drill bushing 28.

The drill motor 38 is then operable to rotate the drill bit 32, moving the drill bit along the coincident central and longitudinal axes toward and into cutting engagement with the femoral head. When the drill hole 40 has been thus formed to the desired depth, the drill motor 38 with the drill bit 32 attached is withdrawn from the drill jig. The drill jig itself is then removed from the femur by reversing the attachment operation which was previously described.

While a preferred embodiment of the invention has been disclosed in detail, it should be understood by those skilled in the art that various modifications may be made to the illustrated embodiment without departing from the scope as described in the specification and defined in the appended claims.

What is claimed is:

1. A hand-held drill jig for locating and maintaining a central axis through a head and an associated neck of a femur enabling a drill hole to be formed in the femoral head oriented to said central axis comprising:

guide means having a bore with a longitudinal axis for guiding movement from a superior position of a drill bit oriented to said central axis toward and into cutting engagement with the femoral head; and positioning means engageable with the femur at spaced locations for rendering said guide means immobile relative to the femur and for aligning the longitudinal axis of said guide means relative to said central axis, said positioning means including:

head positioning means mounted on said guide means engageable at spaced locations with the outer peripheral surface of the femoral head; and neck positioning means mounted on said guide means engageable at spaced locations with the outer peripheral surface of the femoral neck;

said head and said neck positioning means jointly causing said longitudinal axis to be oriented with said central axis when said head positioning means is engaged with the outer peripheral surface of the femoral head and when said neck positioning means is engaged with the outer peripheral surface of the femoral neck.

2. A hand-held drill jig as set forth in claim 1 including:

operating means for selectively moving said head positioning means into engagement with the outer peripheral surface of the femoral head and for selectively moving said neck positioning means into engagement with the outer peripheral surface of the femoral neck.

3. A hand-held drill jig as set forth in claim 2 wherein said guide means includes:

an elongated drill bushing having a longitudinal bore therethrough and extending between a proximal end and a distal end;

wherein said head positioning means includes:

a head cone fixed to said distal end of said drill bushing disposed to engageably receive the femoral head therein;

wherein said neck positioning means includes:

a cross beam extending transversely of the longitudinal axis of said drill bushing and slidably received thereon for movement between said proximal and said distal ends;

a pair of operating arms extending generally parallel to said drill bushing between near and far ends, respectively, and being pivotally mounted intermediate said near and far ends to said cross beam at respectively equal distances in opposite directions from said drill bushing; and opposed gripper members mounted to said far ends of said operating arms for mutually firmly engaging the outer peripheral surface of the femoral neck.

4. A hand-held drill jig as set forth in claim 3 wherein said drill bushing is externally threaded; wherein said operating means includes:

an internally threaded sleeve threadedly engaged with said drill bushing and movable thereon between said proximal and distal ends;

an outer contoured cam surface on said sleeve; and a knob having an external gripping surface for rotating said sleeve and thereby moving said cam surface between said proximal and distal ends of said drill bushing; and wherein said neck positioning means includes:

a cam follower on said near end of each of said operating arms engageable with said cam surfaces;

whereby movement of said sleeve toward said distal end of said drill bushing releases said gripper members from engagement with the outer peripheral surface of the femoral neck and movement of said sleeve toward said proximal end of said drill bushing moves said gripper members toward firm engagement with the outer peripheral surface of the femoral neck.

5. A hand-held drill jig as set forth in claim 3 wherein said head cone includes:

a plurality of legs extending away from said distal end of said drill bushing at circumferentially spaced locations and away from the longitudinal axis of said drill bushing, said legs having inner surfaces generally facing the longitudinal axis, and collectively defining a cavity for engageably receiving the femoral head therein.

* * * * *